United States Patent
Weinberg

(10) Patent No.: US 12,310,881 B2
(45) Date of Patent: May 27, 2025

(54) OSTOMY POUCH WITH VIEWING OPTION FEATURE

(71) Applicant: Hollister Incorporated, Libertyville, IL (US)

(72) Inventor: Robert J. Weinberg, Lake Villa, IL (US)

(73) Assignee: HOLLISTER INCORPORATED, Libertyville, IL (US)

( * ) Notice: Subject to any disclaimer, the term of this patent is extended or adjusted under 35 U.S.C. 154(b) by 0 days.

(21) Appl. No.: 18/556,928

(22) PCT Filed: Jul. 20, 2023

(86) PCT No.: PCT/US2023/070559
§ 371 (c)(1),
(2) Date: Oct. 24, 2023

(87) PCT Pub. No.: WO2024/054724
PCT Pub. Date: Mar. 14, 2024

(65) Prior Publication Data
US 2024/0268987 A1    Aug. 15, 2024

Related U.S. Application Data

(60) Provisional application No. 63/404,750, filed on Sep. 8, 2022.

(51) Int. Cl.
*A61F 5/445*    (2006.01)
*A61F 5/44*     (2006.01)

(52) U.S. Cl.
CPC ............ *A61F 5/445* (2013.01); *A61F 5/4404* (2013.01)

(58) Field of Classification Search
CPC ................... B65D 5/10; B65D 5/2057; B65D 2571/0016; B65D 27/22
See application file for complete search history.

(56) References Cited

U.S. PATENT DOCUMENTS

| 3,570,490 | A | 3/1971 | Berger |
| 3,651,935 | A * | 3/1972 | Nysten .................. B65D 27/22 206/380 |
| 8,574,207 | B2 | 11/2013 | Lundholt et al. |
| 2009/0234312 | A1 | 9/2009 | Toole et al. |

(Continued)

FOREIGN PATENT DOCUMENTS

| EP | 3733137 A1 | 11/2020 |
| EP | 2950760 B1 | 2/2021 |

(Continued)

OTHER PUBLICATIONS

International Search Report issued by ISA/EPO in connection with PCT/US2023/070559 dated Oct. 6, 2023.

(Continued)

*Primary Examiner* — Rebecca E Eisenberg
*Assistant Examiner* — Matthew Wrubleski
(74) *Attorney, Agent, or Firm* — Klintworth & Rozenblat IP LLP

(57) ABSTRACT

An ostomy pouch for collecting body waste includes a flap formed from a cutout of an outer layer of the ostomy pouch. The flap covers a viewing option for viewing a stoma and an interior of the ostomy pouch. The flap includes a tab attached to the outer layer. The tab is configured to secure the flap closed.

18 Claims, 7 Drawing Sheets

(56) References Cited

U.S. PATENT DOCUMENTS

2021/0100678 A1 4/2021 Hoggarth et al.
2021/0353448 A1 11/2021 Fattman et al.
2021/0369493 A1 12/2021 Young et al.
2021/0369494 A1 12/2021 Holden et al.

FOREIGN PATENT DOCUMENTS

WO       2021165703 A1     8/2021
WO     WO-2021165705 A1 *   8/2021  ........... A61F 5/4404

OTHER PUBLICATIONS

Written Opinion issued by ISA/EPO in connection with PCT/US2023/070559 dated Oct. 6, 2023.

* cited by examiner

OSTOMY POUCH WITH VIEWING OPTION FEATURE

This is a National Stage Application of International Patent Application No. PCT/US2023/070559, filed Jul. 20, 2023, which claims the benefit of and priority to U.S. Provisional Application No. 63/404,750, filed Sep. 8, 2022, the entireties of which are incorporated fully herein by references.

BACKGROUND

The present disclosure pertains to an ostomy pouch. More particularly, the present disclosure pertains to an ostomy pouch with a viewing option feature.

Ostomy pouches for collecting body waste are used by patients who have had surgery such as a colostomy, ileostomy, or urostomy. Ostomy pouches typically include flat, opposing side walls secured together along their edges to define a collection cavity. One of the side walls is provided with an opening to receive a stoma, and means to secure the pouch to the user, such as an adhesive barrier, so that body waste discharged through the stoma is received within the cavity.

In order to determine whether an ostomy bag is installed properly or to inspect a stoma, a user or clinician may wish to view the stoma while the ostomy pouch is secured to the user. Similarly, the body waste discharge may also need to be inspected while the ostomy pouch is secured to the user. However, for privacy reasons, the stoma and interior of the pouch must be securely covered from view when they are not being examined. Thus, it is desirable to provide an ostomy pouch system, including a view option and cover.

Accordingly, there is a need for an improved ostomy pouch with a view option that can be securely covered.

BRIEF SUMMARY

An ostomy pouch, including a flap and viewing option is provided according to various embodiments.

In one aspect, the ostomy pouch may include a body side wall and a distal wall joined along their peripheral edges to define a cavity therebetween for collecting body waste, an inlet opening defined in the body side wall configured to receive a stoma, and an outer layer attached to and covering the distal wall. The outer layer may include a flap formed by a cutout of the outer layer. The cutout may align with the inlet opening and may define a viewing option, such as a viewing window, for the stoma and the contents of the pouch. The flap may include a tab configured to secure the flap in a closed position.

In an embodiment, at least a portion of the distal wall may be formed from a transparent material and the outer layer may be formed from an opaque material.

In some embodiments, the outer layer may include a slot configured to receive the tab.

In an embodiment, the tab may be formed from a semi-rigid material and comprises an end with a width greater than a width of the slot.

In another embodiment, the tab may be attached to a body-side of the outer layer.

In an embodiment, the tab may be configured to insert into the slot from a distal side of the outer layer.

In an embodiment, the outer layer may include a distal comfort panel.

In another aspect, the ostomy pouch may include a body side wall and a distal wall joined along their peripheral edges to define a cavity therebetween for collecting body waste, an inlet opening defined in the body side wall configured to receive a stoma, an outer layer attached to and covering the distal wall, and a window cover attached to the outer layer. The outer layer may include a viewing window that aligns with the inlet opening for viewing the stoma. The window cover aligns with the viewing window. The window cover may include a tab configured to secure the window cover in a closed position.

In an embodiment, at least a portion of the and window cover may be formed from a transparent material and the outer layer may be formed from an opaque material.

In some embodiments, the outer layer may include a slot configured to receive the tab.

In an embodiment, the tab may be formed from a semi-rigid material and comprises an end with a width greater than a width of the slot.

In another embodiment, the tab may be attached to a body-side of the window cover.

In an embodiment, the tab may be configured to insert into the slot from a distal side of the outer layer.

In an embodiment, the outer layer may include a distal comfort panel.

The foregoing general description and the following detailed description are examples only and are not restrictive of the present disclosure.

BRIEF DESCRIPTION OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 1:
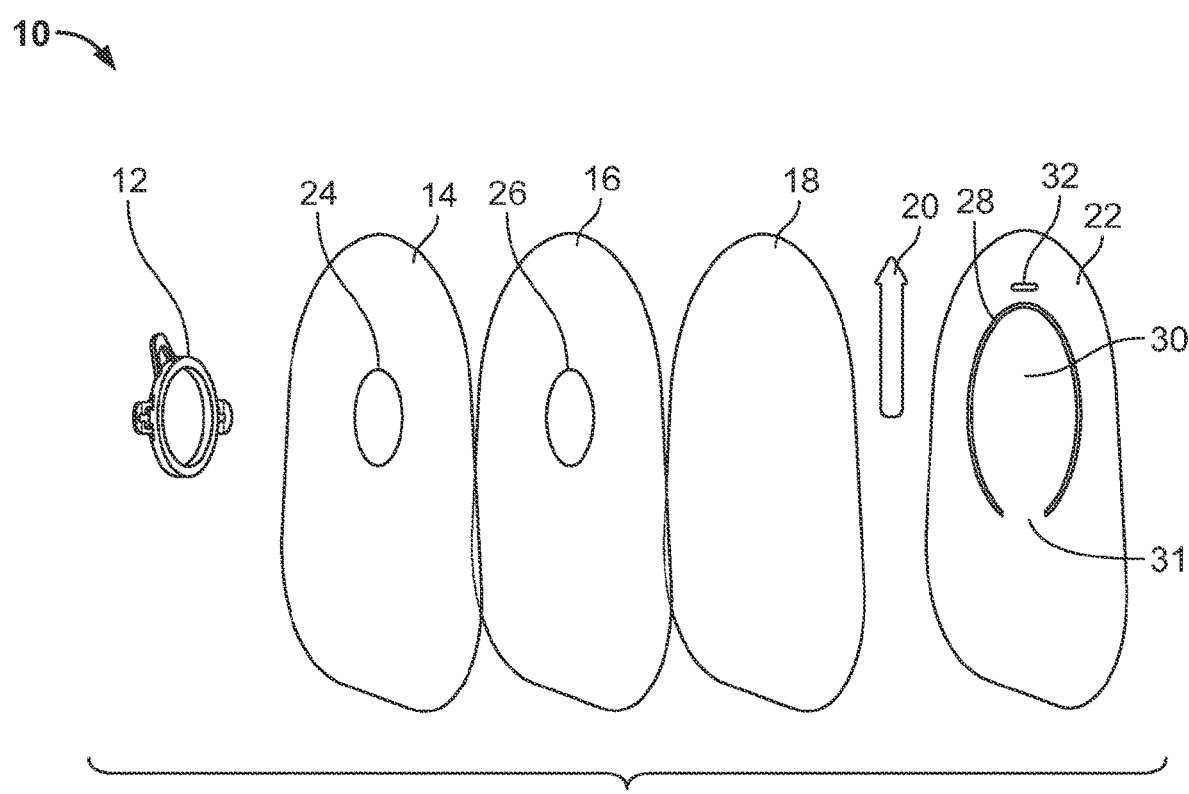
FIG. 1 is an exploded view of an ostomy pouch according to an embodiment.

While the present disclosure is susceptible of embodiment in various forms, there is shown in the drawings and will hereinafter be described presently preferred embodiments with the understanding that the present disclosure is to be considered an exemplification and is not intended to limit the disclosure to the specific embodiments illustrated. The words "a" or "an" are to be taken to include both the singular and the plural. Conversely, any reference to plural items shall, where appropriate, include the singular. The words "first," "second," "third," and the like may be used in the present disclosure to describe various information, such information should not be limited to these words. These words are only used to distinguish one category of information from another. The directional words "top," "bottom,"

up," "down," front," "back," and the like are used for purposes of illustration and as such should not be limiting. Depending on the context, the word "if" as used herein may be interpreted as "when" or "upon" or "in response to determining."

The present disclosure provides an ostomy pouch that includes a viewing option, such as a viewing window, and a securement system. The viewing option may include a cover, such as a viewing flap, and can include at least one tab for the flap for securely covering the viewing window.

Referring now to the figures, FIGS. 1-7 show an ostomy pouch 10 according to an embodiment. The ostomy pouch 10 generally includes a user attachment device 12, a body side comfort panel 14, a body side wall 16, a distal wall 18, a tab member 20, and a distal comfort panel 22.

FIG. 1 is an exploded view of the ostomy pouch 10. The body side wall 16 and the distal wall 18 may be sealed along their peripheral edges to define a cavity therein for collecting stoma output. The body side comfort panel 14 may be attached to the body side wall 16. The body side comfort panel 14 includes a first opening 24, and the body side wall 16 includes a second opening 26. The first and second openings 24, 26 define an inlet opening and may be aligned and configured to receive a stoma (not shown).

The distal comfort panel 22 may be attached to the distal wall 18. The distal wall 18 is formed from a transparent or translucent material to allow for viewing the stoma and the contents of the pouch 10. The distal comfort panel 22 can include a cutout that forms a viewing opening or viewing window 28 and forms a viewing flap 30. The flap 30 can include a portion such as a hinge portion 31 that remains attached to the distal comfort panel 22 to allow for opening the flap 30 to view the stoma and contents of the pouch 10, and to allow for closing the flap 30 for privacy. The distal comfort panel can further include a slot 32 configured to receive the tab member 20.

In an embodiment, the distal comfort panel 22 may be an outer layer.

In another embodiment, the distal comfort panel 22 can include a viewing window and a window cover. The window cover can be attached to the distal comfort panel 22 and can align with the viewing window. The window cover can include a tab for securing the window cover in a closed position.

Figure 2:
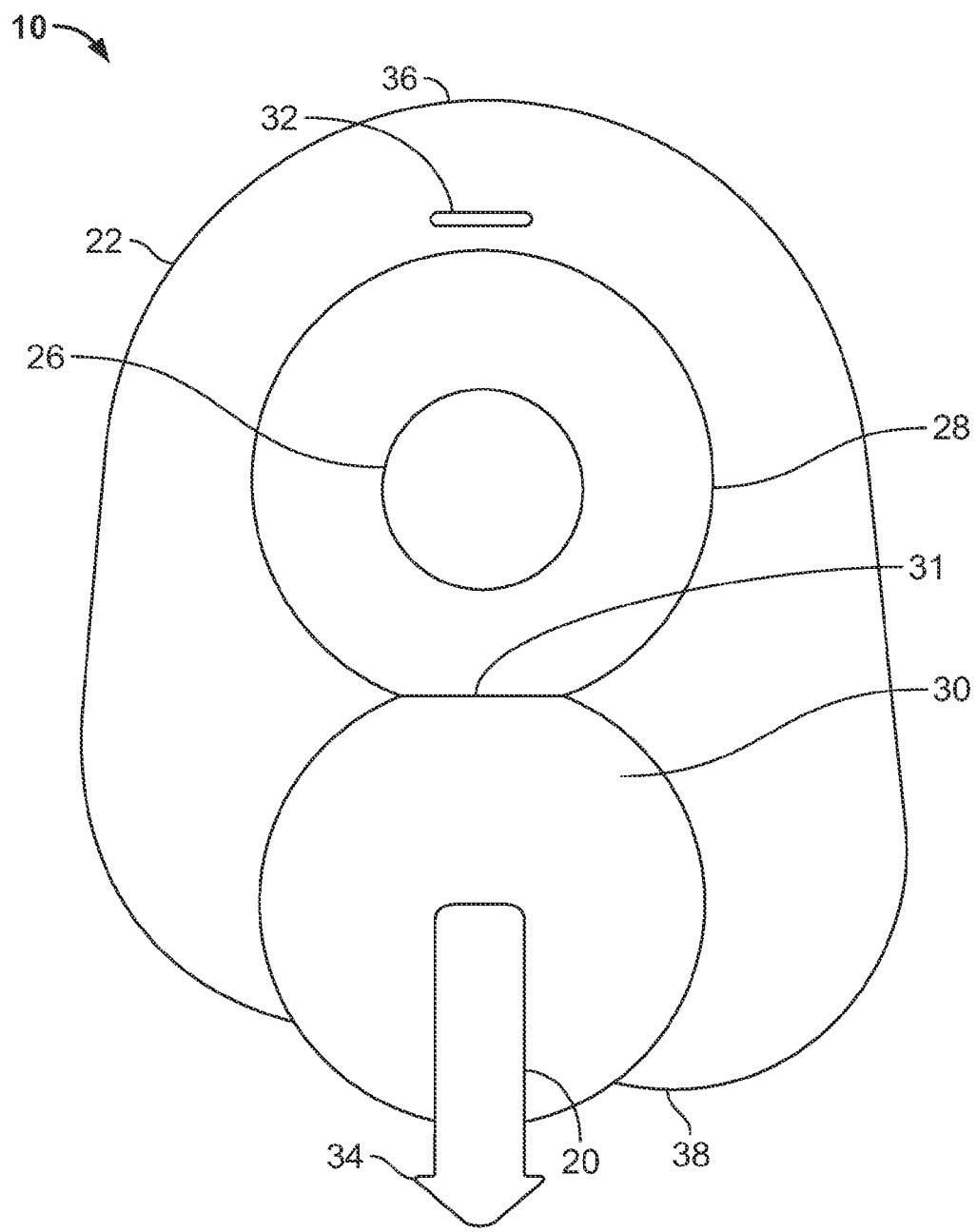
FIG. 2 is a distal view of the ostomy pouch of FIG. 1 with a viewing flap in an open state.

FIG. 2 shows a distal view of the ostomy pouch 10 with the flap 30 in an open position. In the open position, the viewing opening or window 28 is exposed and the stoma and the contents of the ostomy pouch 10 may be viewed.

In this embodiment, the tab member 20 may be attached to the body side of the distal comfort panel 22. Other locations for attaching the tab member 20 will be appreciated by those skilled in the art and are within the scope and spirit of the present disclosure. The tab member 20 can include a tab end 34. The tab end 34 is configured to be inserted into the slot 32.

The ostomy pouch 10 includes an upper end 36 and a lower end 38. The upper end 36 can be located closer to the inlet opening relative to the lower end 38. The lower end 38 is configured to receive body waste discharged from the stoma.

In an embodiment, the hinge portion 31 may be positioned near the lower end 38 and the slot may be positioned opposite the hinge portion 31 near the upper end 36. In this embodiment, the flap 30 opens downward, towards the lower end 38 of the pouch 10 when it is in the open position. In other embodiments, the hinge portion 31 may be positioned near the upper end 36 so that the flap 30 opens upwardly, or between the upper and lower ends 36, 38 so that the flap 30 opens to the side. In such embodiments, the slot 32 is positioned opposite the hinge portion 31 so that the flap 30 can be securely closed.

Figure 7:
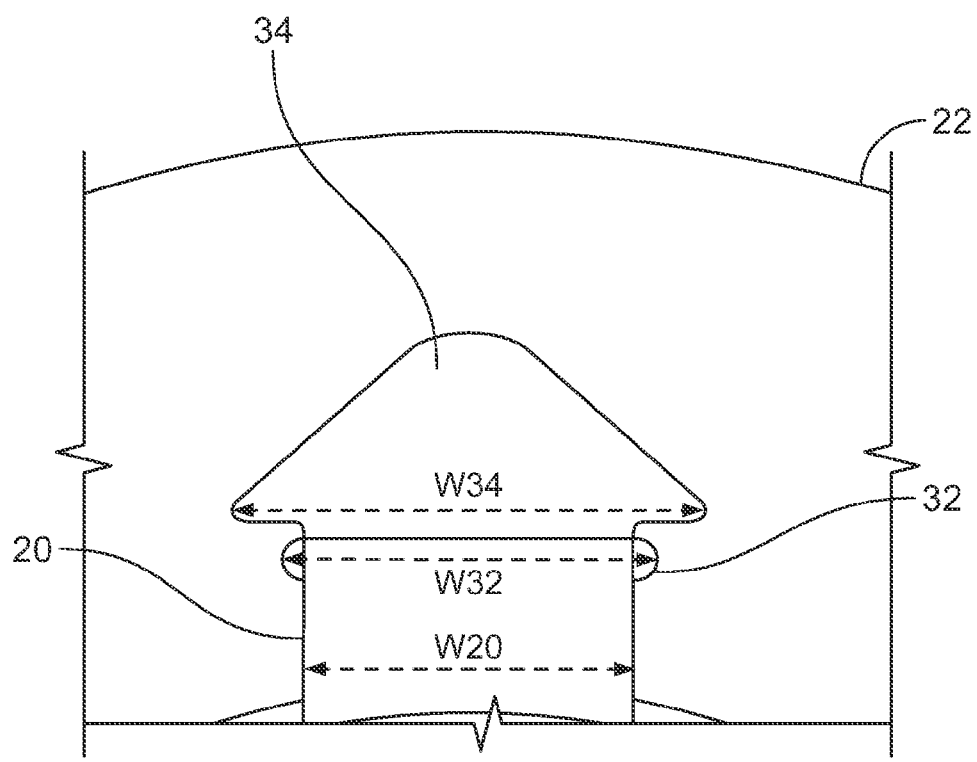
FIG. 7 is a partially enlarged view of the tab of the ostomy pouch of FIG. 6 with the transparent outer layer and the viewing flap closed and secured.

The tab end 34 has a width W34 that is larger than a width W32 of the slot 32 (FIG. 7). In an embodiment, the tab end 34 has an arrowhead shape, having a head to facilitate inserting the tab end 34 into and securing the tab end 34 in the slot 32.

Figure 3:
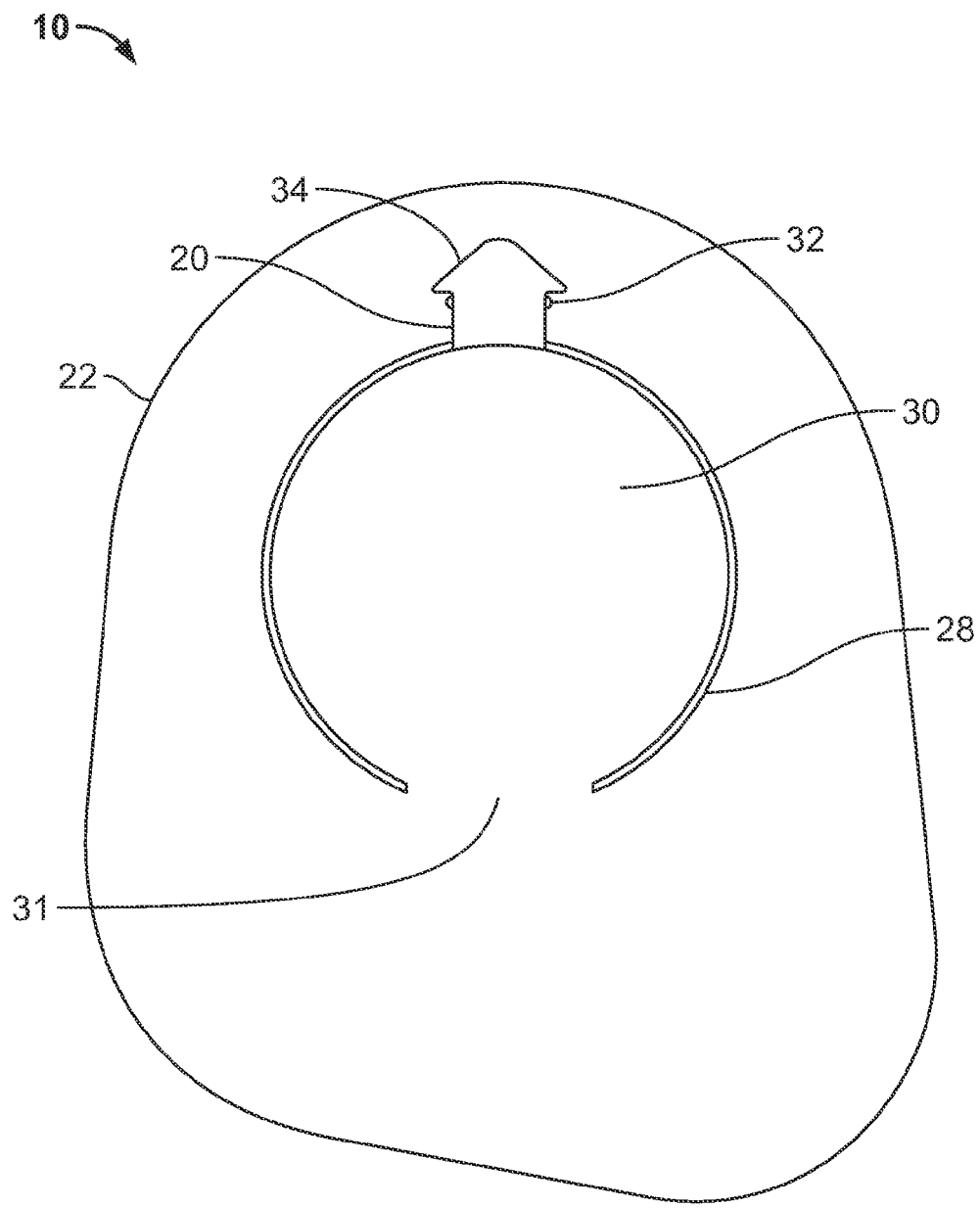
FIG. 3 is a distal view of the ostomy pouch of FIG. 1 with the viewing flap closed.

FIG. 3 shows a distal view of the ostomy pouch 10 with the flap 30 closed. In the closed position, the flap 30 covers the viewing window 28 and the stoma and the contents of the ostomy pouch 10 may not be viewed. The tab end 34 is not inserted into slot 32 and therefore, the flap 30 is not secured.

Figure 4:
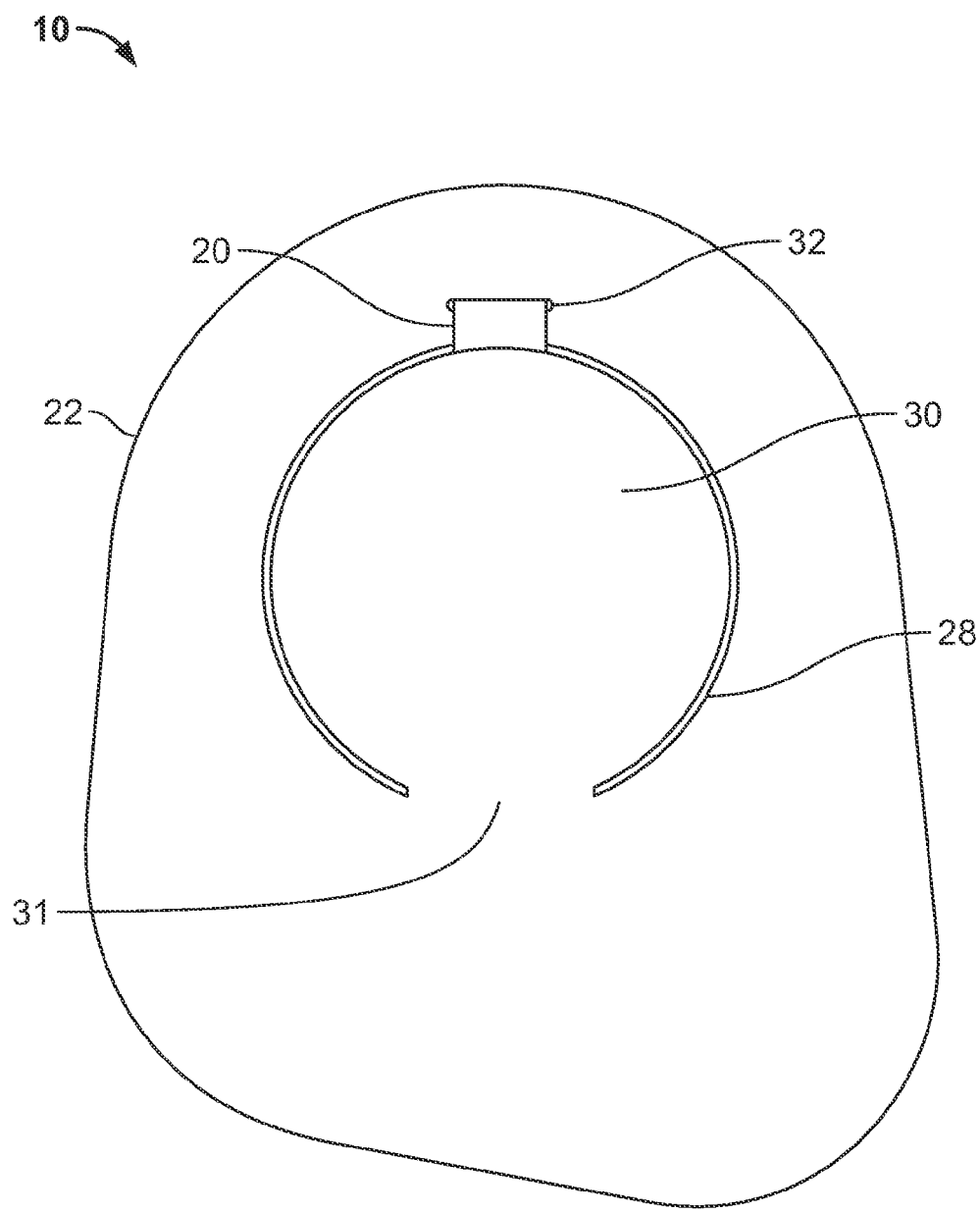
FIG. 4 is a distal view of the ostomy pouch of FIG. 1 with the viewing flap closed and secured.

FIG. 4 shows a distal view of the ostomy pouch 10 with the flap 30 closed and secured. In the secured position, the tab end 34 (not shown) is inserted into the slot 32. The flap 30 cannot be opened without removing the tab end 34 from the slot 32.

Figure 5:
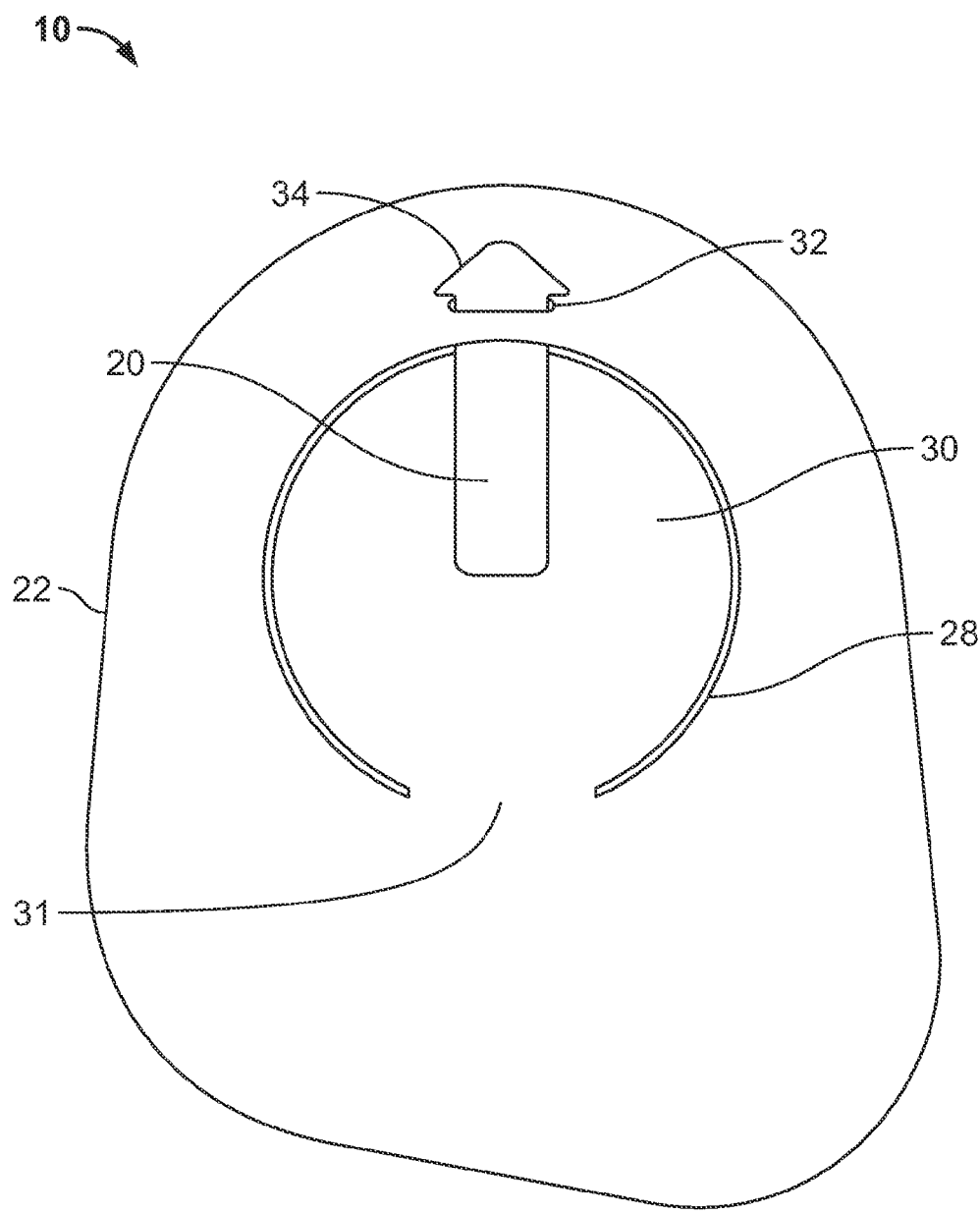
FIG. 5 is a body-side view of an outer wall or side of the ostomy pouch of FIG. 1 with a closed and secured viewing flap.

FIG. 5 shows a body view of the distal comfort panel 22 with the flap 30 closed and secured. The tab member 20 is attached to the body side of the distal comfort panel 22. The tab end 34 is inserted through, and extends out of, the slot 32.

Figure 6:
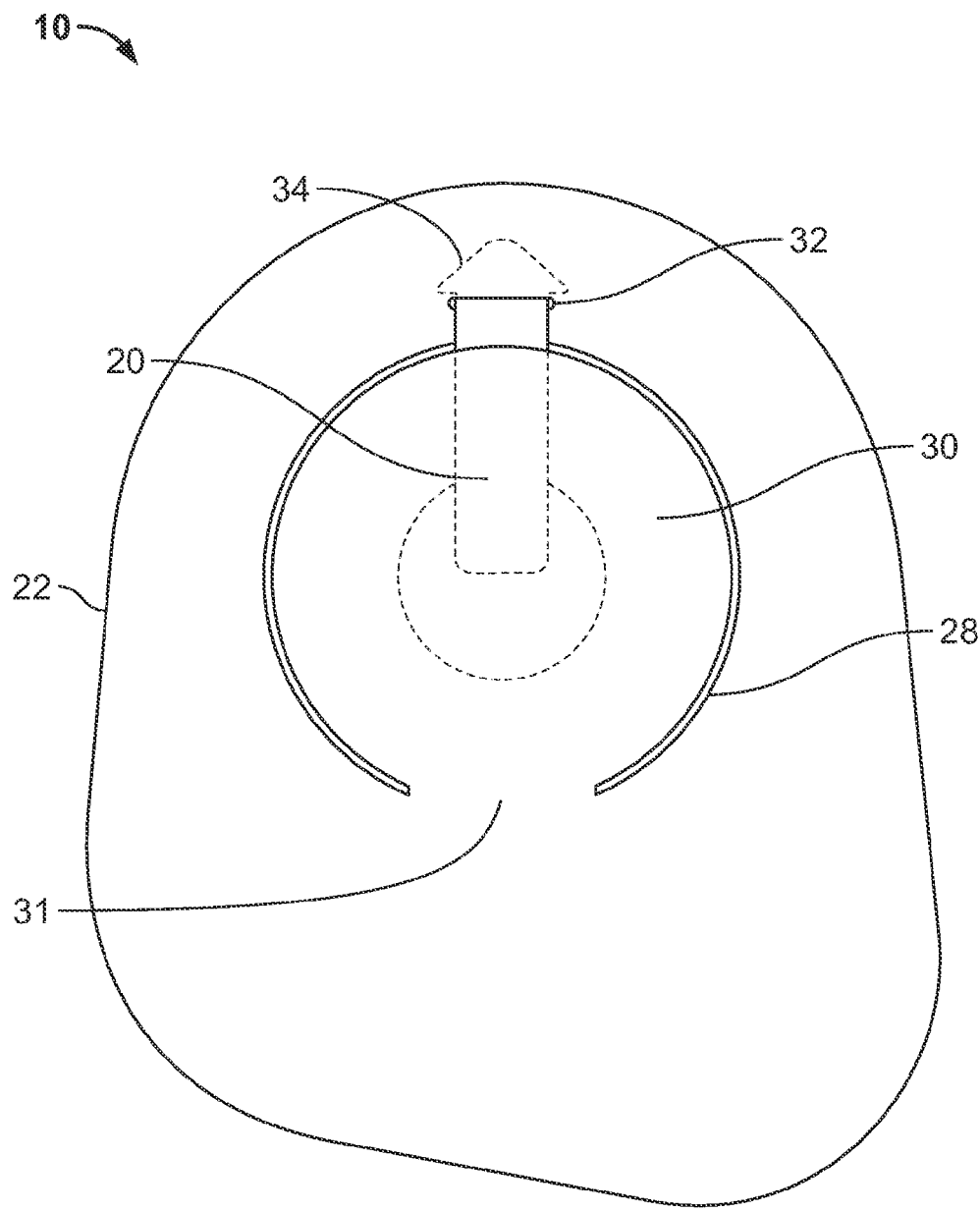
FIG. 6 is a distal view of the ostomy pouch of FIG. 1 with a transparent outer layer and a closed and secured viewing flap.

FIG. 6 shows a distal view of the ostomy pouch 10 with a transparent distal comfort panel 22 and the flap 30 in a closed position and secured. The portions of the tab member 20 that are arranged between the flap 30 and the distal wall of the pouch 18 and between the distal comfort panel 22 and the distal wall of the pouch 18 are shown in dash lines.

FIG. 7 shows a distal view of the ostomy pouch 10 with the flap 30 closed and secured. The tab end 34 is inserted into the slot 32. In this embodiment, the tab end 34 has a width W34 that is larger than the width W20 of the tab member 20. The width W32 of the slot 32 is slightly larger than the width W20 of the tab member 20, but is slightly smaller than the width W34 of the tab end 34. The tab end 34 can be made out of a semi-rigid material that allows the tab end 34 to bend and be inserted into slot 32 but remain within the slot 32.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. An ostomy pouch comprising: a body side wall and a distal wall joined along their peripheral edges to define a cavity therebetween for collecting body waste;
  an inlet opening defined in the body side wall configured to receive a stoma; and
  an outer layer attached to and covering an entire surface of the distal wall, the outer layer comprising:
    a flap integrally formed with the outer layer by a cutout in the outer layer; and
    a hinge portion defined by an uncut portion in the outer layer, wherein the flap remains attached to the outer layer via the hinge portion, wherein the cutout aligns with the inlet opening and defines a viewing window for the stoma, and wherein the flap includes a tab configured to secure the flap in a closed position and wherein the cutout is positioned to not reach a peripheral edge of the outer layer.

2. The ostomy pouch of claim 1, wherein at least a portion of the distal wall is formed from a transparent material and the outer layer is formed from an opaque material.

3. The ostomy pouch of claim 1, wherein the outer layer comprises a slot configured to receive the tab.

4. The ostomy pouch of claim 3, wherein the tab is formed from a semirigid material and comprises an end with a width greater than a width of the slot.

5. The ostomy pouch of claim 1, wherein the tab is attached to a body-side of the outer layer.

6. The ostomy pouch of claim 3, wherein the tab is configured to insert into the slot from a distal side of the outer layer.

7. The ostomy pouch of claim 1, wherein the outer layer comprises a distal comfort panel.

8. The ostomy pouch of claim 3, wherein the tab is positioned within the slot to secure the flap in the closed position, and wherein removing the tab from the slot places the flap in the open position.

9. The ostomy pouch of claim 1, wherein the outer layer is formed of a single panel.

10. An ostomy pouch comprising:
   a body side wall and a distal wall joined along their peripheral edges to define a cavity therebetween for collecting body waste;
   an inlet opening defined in the body side wall configured to receive a stoma;
   an outer layer attached to and covering an entire surface of the distal wall, the outer layer comprising:
      a viewing window aligned with the inlet opening for viewing the stoma, wherein the viewing window is formed by a cutout of the outer layer;
      a hinge portion defined by an uncut portion in the outer layer; and
      a window cover formed in the outer layer, wherein the window cover remains attached to the outer layer by the hinge portion, wherein the window cover aligns with the viewing window, and wherein the window cover further comprises includes a tab configured to secure the window cover in a closed position
   and wherein the cutout is positioned to not reach a peripheral edge of the outer layer.

11. The ostomy pouch of claim 10, wherein at least a portion of the distal wall is formed from a transparent material and the outer layer and window cover are formed from an opaque material.

12. The ostomy pouch of claim 10, wherein the outer layer comprises a slot configured to receive the tab.

13. The ostomy pouch of claim 12, wherein the tab is formed from a semirigid material and comprises an end with a width greater than a width of the slot.

14. The ostomy pouch of claim 10, wherein the tab is attached to a body-side of the window cover.

15. The ostomy pouch of claim 12, wherein the tab is configured to insert into the slot from a distal side of the outer layer.

16. The ostomy pouch of claim 10, wherein the outer layer comprises a distal comfort panel.

17. The ostomy pouch of claim 12, wherein the tab is positioned within the slot to secure the window cover in the closed position, and wherein removing the tab from the slot places the window cover in the open position.

18. The ostomy pouch of claim 12, wherein the outer layer is formed of a single panel.

* * * * *